(12) United States Patent  (10) Patent No.: US 7,316,702 B2
Joergensen et al.  (45) Date of Patent: Jan. 8, 2008

(54) METHODS AND APPARATUS FOR DISTAL PROTECTION DURING A MEDICAL PROCEDURE

(75) Inventors: Ib Erling Joergensen, Haigerloch (DE); Gerd Seibold, Ammerbuch (DE); Bodo Stefan Josef Quint, Rottenburg (DE); Kenneth J. Michlitsch, Livermore, CA (US); Martina Bremser, Rottenburg (DE); Randolf Von Oepen, Tuebingen (DE)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 703 days.

(21) Appl. No.: 10/622,918

(22) Filed: Jul. 18, 2003

(65) Prior Publication Data
US 2004/0098026 A1 May 20, 2004

Related U.S. Application Data

(63) Continuation of application No. 09/957,482, filed on Sep. 19, 2001, now Pat. No. 6,616,682.

(51) Int. Cl.
*A61M 29/00* (2006.01)
(52) U.S. Cl. .................................... 606/200
(58) Field of Classification Search ............. 606/113, 606/114, 159, 127, 200
See application file for complete search history.

(56) References Cited

U.S. PATENT DOCUMENTS

| | | |
|---|---|---|
| 4,723,549 A | 2/1988 | Wholey et al. |
| 4,873,978 A | 10/1989 | Ginsburg |
| 5,108,419 A | 4/1992 | Reger et al. |
| 5,192,290 A | 3/1993 | Hilal |
| 5,411,509 A | 5/1995 | Hilal |
| 5,695,519 A | 12/1997 | Summers et al. |
| 5,725,568 A | 3/1998 | Hastings |
| 5,769,816 A | 6/1998 | Barbut et al. |
| 5,814,064 A | 9/1998 | Daniel et al. |
| 5,827,304 A | 10/1998 | Hart |
| 5,827,324 A | 10/1998 | Cassell et al. |
| 5,837,140 A | 11/1998 | Fini et al. |
| 5,941,869 A | 8/1999 | Patterson et al. |
| 6,010,531 A | 1/2000 | Donlon et al. |
| 6,152,946 A | 11/2000 | Broome et al. |
| 6,152,947 A | 11/2000 | Ambrisco et al. |
| 6,165,200 A | 12/2000 | Tsugita et al. |
| 6,179,859 B1 | 1/2001 | Bates et al. |
| 6,336,934 B1 | 1/2002 | Gilson et al. |
| 6,361,545 B1 * | 3/2002 | Macoviak et al. .......... 606/200 |

* cited by examiner

*Primary Examiner*—Kevin T. Truong
(74) *Attorney, Agent, or Firm*—Franco A. Serafini, Esq.; Luce, Forward, Hamilton & Scripps LLP

(57) ABSTRACT

Apparatus and methods for providing distal protection during a medical procedure comprising a vascular filter having a self-expanding, porous foam body that conformably seals against a vessel wall and captures emboli within one or more recesses. The filter is coupled to a distal region of an elongated member, such as a guide wire. Delivery systems for use with filters of the present invention and methods of using the apparatus of the present invention also are provided.

25 Claims, 4 Drawing Sheets

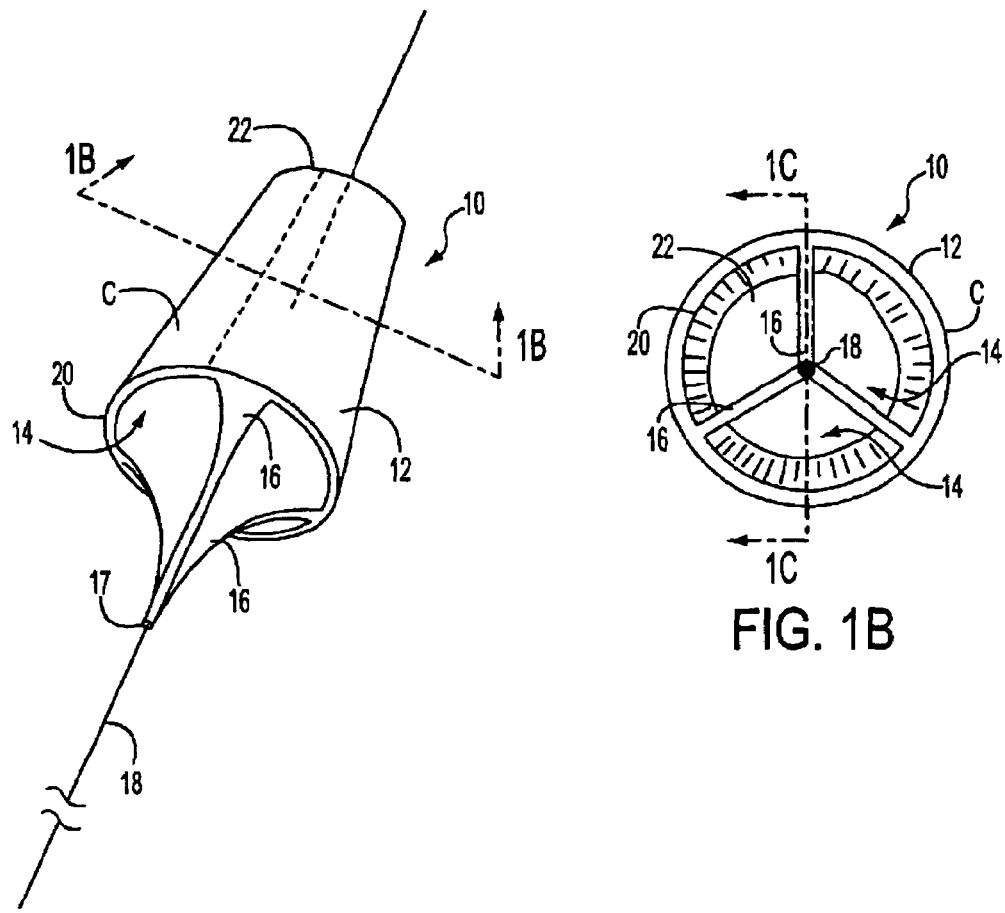
FIG. 1A
FIG. 1B
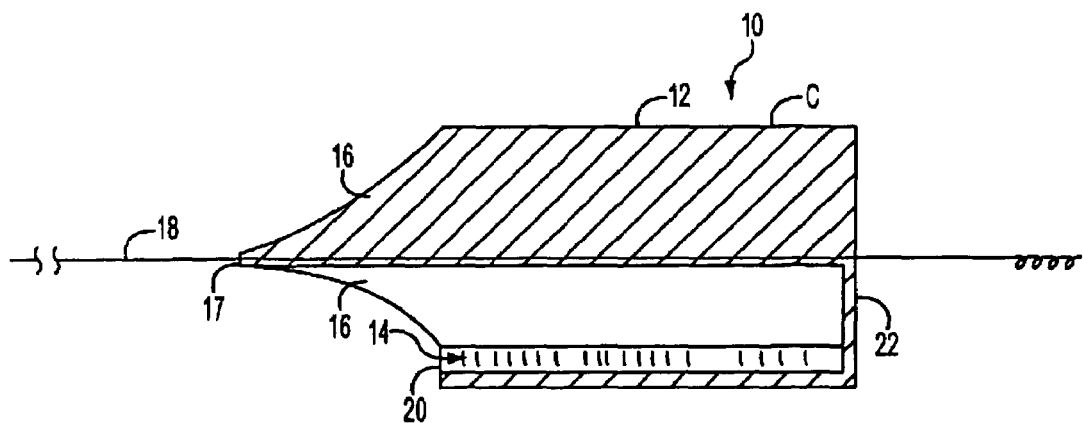
FIG. 1C

METHODS AND APPARATUS FOR DISTAL PROTECTION DURING A MEDICAL PROCEDURE

FIELD OF THE INVENTION

The present invention relates to methods and apparatus for filtering material from a body lumen. More particularly, the present invention provides a resiliently self-expanding foam filter adapted to capture and remove emboli, thrombus, and foreign bodies from a patient's vasculature.

BACKGROUND OF THE INVENTION

Percutaneous interventional procedures to treat occlusive vascular disease, such as angioplasty, atherectomy and stenting, often dislodge material from the vessel walls. This dislodged material, known as emboli, enters the bloodstream, and may be large enough to occlude smaller downstream vessels, potentially blocking blood flow to tissue. If the blockage occurs in critical tissue, such as the heart, lungs, or brain, resulting ischemia poses a serious threat to the health or life of a patient.

Additionally, the deployment of stents and stent-grafts to treat aneurysms, ruptures, and other vascular diseases may result in the formation of clots or emboli. Such particulate matter also may cause infarction or stroke if released into the bloodstream. Furthermore, interventional procedures may generate foreign bodies that are left within a patient's bloodstream, thereby endangering the life of the patient. Foreign bodies may include, for example, a broken guide wire, pieces of a stent, or pieces of a catheter.

Numerous previously known methods and apparatus have been proposed to reduce complications associated with embolism, thrombus release, or foreign body material generation. U.S. Pat. No. 5,814,064 to Daniel et al. describes an emboli filter system having a radially expandable mesh filter disposed on the distal end of a guide wire. The filter is deployed distal to a region of stenosis, and any interventional devices, such as angioplasty balloons or stent delivery systems, are advanced along the guide wire. The filter is designed to capture emboli generated during treatment of the stenosis while permitting blood to flow through the filter. Similar filter systems are described in U.S. Pat. No. 4,723,549 to Wholey et al. and U.S. Pat. No. 5,827,324 to Cassell et al.

One disadvantage common to many prior art radially expandable filter systems, such as those described in the foregoing patents, is the number of parts necessary to fabricate the devices. Connecting more than a minimal number of such parts to a guide wire generally increases delivery complications. The ability of the guide wire to negotiate tortuous anatomy is reduced, and the profile of the device in its delivery configuration increases. Consequently, it may be difficult or impossible to use such devices in small diameter vessels, such as are commonly found in the carotid and coronary arteries, as well as in cerebral vasculature. Moreover, such filter devices are often incapable of preventing material from escaping from the filter during the process of collapsing the filter for removal.

Thus, there has been a long-felt need in the art for a simple, safe, and effective emboli filter that does not significantly impede antegrade blood flow, that reduces stress applied to the vessel wall, that conforms to the size and internal profile of the vessel in vivo to reduce escape of emboli past the filter, that may be collapsed for retrieval without loss of captured emboli, that may be sized for use in small vasculature, and that may be used in tortuous anatomy without increased delivery complications.

Foams are used in a variety of vascular medical applications. For example, U.S. Pat. No. 5,725,568 to Hastings describes the use of biocompatible foam as an occlusive agent during aneurysm repair. U.S. Pat. No. 5,837,140 to Fini et al. describes a blood filter fabricated from polyurethane foam. The filter is contained within a semirigid housing and is configured for use as part of an extracorporeal blood circuit. It is not suited for intravascular use.

U.S. Pat. Nos. 5,192,290 and 5,411,509 to Hilal, as well as U.S. Pat. No. 5,827,304 to Hart, describe embolectomy catheters having a portion comprising an expandable elastomeric foam that may be used to remove blood clots from a patient's vessel. These foam portions are substantially spherical and presumably occlude or impede antegrade flow through the vessel; they are therefore not suited for use as emboli filters.

U.S. Pat. No. 6,152,947 to Ambrisco et al. describes an embolic filter having a plastic or metal frame attached to a filter mesh. Foam seals may be attached to the frame so that the frame conforms to and sealingly engages the patient's vasculature. While foam seals may reduce emboli leakage around an embolic filter and may be less traumatic to vascular intima, as compared to other previously known filters, foam seals are an additional component that is expected to increase delivery profile and increase delivery complications. That patent states at column 3, lines 15-16, that the filter frame itself "may be metal, plastic, gel or foam or any combination thereof," but provides no teaching as to how a filter frame fabricated exclusively from foam could be made or would function. Furthermore, Ambrisco does not describe a filter mesh fabricated from foam.

U.S. Pat. No. 6,010,531 to Donlon et al. describes a catcher adapted for placement in a patient's left ventricle during aortic valve replacement surgery to catch any debris released during leaflet removal, or in the debridement process. The catcher comprises a flexible, porous mesh, foam, gauze, or screen constructed as a bag or pouch with an opening on the top end. A flexible and resilient metal or elastomeric ring may be mounted to the catcher around the opening to allow the ring to collapse for delivery and to expand to engage the ventricular wall. The catcher is attached to a tether, such as a suture, to facilitate positioning within the ventricle.

Donlon's catcher device has several drawbacks that make it unsuitable for use as a vascular filter. The catcher is not disposed about a guide wire. It is not sized for use in small vasculature, and the metal or elastomeric ring mounted to the catcher would presumably kink if sized for such use. Furthermore, the metal ring would apply a potentially traumatic stress against the vessel wall.

U.S. Pat. No. 5,941,869 to Patterson et al. describes an embolic filter having a plurality of structural members that enclose and support a nonthrombogenic expandable filter medium. The structural members are made of metal or a polymer, and the expandable filter medium may be a porous foam material. As with previous filter devices, it is expected that the substantially rigid structural members will apply a stress to the vessel wall that may damage or traumatize the wall.

U.S. Pat. No. 6,165,200 to Tsugita et al. describes a filter assembly having a plurality of substantially cylindrical, expandable sponge-like elements that are adapted to engage the wall of a patient's vessel. The sponge-like elements are affixed to a guide wire and have sufficient porosity to allow blood, but not large emboli, to pass freely therethrough.

Additionally, the sponge-like elements may have varying porosity that decreases along the length of the guide wire, so that embolic material enters a proximal portion of the elements, but is captured within a distal portion of the elements. The patent claims that varying porosity along the length of the guide wire substantially decreases a likelihood that embolic material will be caught only on an outer surface of the sponge-like elements, thus reducing the risk that emboli will be released when the sponge-like elements are retrieved within a sheath.

While it is expected that the filter assembly of the Tsugita patent will sealingly conform to the patient's vessel with reduced trauma or injury, the assembly has several drawbacks. Applicants disagree with the assertion in the Tsugita patent that varying porosity will substantially reduce the risk of emboli being liberated during retrieval. Red blood cells have an approximate diameter of 5 microns. Dangerous emboli, meanwhile, are commonly defined as particles greater than about 60-100 microns in diameter. Dangerous emboli, however, can vary in size as much as an order of magnitude. Thus, unless a very substantial variance in porosity is provided (a variance not feasible for sponge-like elements suitable used in small vasculature), it is expected that the largest and potentially most dangerous emboli may not, or may only partially, enter within the pores rather than be caught against an outer surface of the sponge-like elements. During retrieval, some or a portion or all of these larger particles may escape into the blood stream.

Providing a plurality of sponge-like devices as in the Tsugita patent is expected to have a number of drawbacks. First, a longer length of vessel is required to deploy the multiple sponge-like elements. Second, an increased risk of complications, e.g. snagging or frictional sticking, exists while collapsing the long length of sponge-like elements back to the delivery configuration. Third, the plurality of sponge-like elements reduces trackability through tortuous anatomy. Fourth, the length of the sponge-like elements, coupled with their density, is expected to reduce the pressure of blood passing through the elements, thus potentially causing ischemia or damage to downstream tissue. The density and length of the sponge-like elements also may require a volume of material to fabricate the cylinders that renders disposal of the elements within a delivery sheath having a delivery profile suited for small vasculature, for example, a delivery profile as small as 3 Fr, unfeasible.

An additional drawback of the sponge-like elements is that, even if dangerous emboli are captured within the pores, the emboli may be squeezed out of the pores during collapse of the elements back to the delivery configuration. This risk is especially acute due to the deployed, cylindrical profile of the sponge-like elements. The profile provides a sharp step, or discontinuity, to a retrieval sheath that is expected to increase retrieval complications.

In view of the foregoing disadvantages of previously known apparatus and methods, it would be desirable to provide a vascular filter that overcomes such disadvantages and employs few components.

It would be desirable to provide a vascular filter that conforms, and reduces a risk of trauma, to the vessel wall.

It also would be desirable to provide a vascular filter that is capable of being contracted to a small delivery profile, thus permitting use of the filter in small vessels.

It still further would be desirable to provide a vascular filter that reduces a risk of emboli or thrombus removed from the vessel wall escaping from the filter when the filter is collapsed and removed.

It would be desirable to provide a vascular filter that does not significantly impede antegrade blood flow.

It would be desirable to provide a vascular filter having a filter element fabricated solely from foam.

SUMMARY OF THE INVENTION

In view of the foregoing, it is an object of the present invention to provide a vascular filter that overcomes disadvantages of previously known vascular filters and foreign body removal devices, and employs few components.

It is an object of the present invention to provide a vascular filter that conforms, and reduces a risk of trauma, to the vessel wall.

It also is an object of this invention to provide a vascular filter that is capable of being contracted to a small delivery profile, thus permitting use of the device in small vessels.

It is another object to provide a vascular filter that reduces a risk of emboli or thrombus removed from the vessel wall escaping from the filter when the device is collapsed and removed.

It is yet another object to provide a vascular filter that does not significantly impede antegrade blood flow.

It is an object to provide a vascular filter having a filter element fabricated solely from foam. These and other objects of the present invention are accomplished by providing a vascular filter fabricated from foam that is suited for both conformably sealing against a vessel wall and for capturing emboli within one or more recesses. The foam is preferably porous with a pore size that allows blood, but not dangerously-sized emboli, to pass therethrough.

Porosity of the foam may be specified to control a pressure drop across the vascular filter. The foam also is elastomeric, allowing the filter to self-expand from a collapsed delivery configuration to an expanded deployed configuration. The foam filter is attached to a distal region of an elongated member, such as a guide wire.

Advantageously, use of foam permits vascular filters constructed in accordance with the present invention to be contracted to very small diameters for delivery without a delivery catheter, or with delivery catheters having diameters as small as 3 Fr. Delivery catheters that permit a lesion to be crossed with an unencumbered guide wire prior to passage of the foam filter may be provided. Such catheters may be configured for "rapid exchange" use. When delivered without a delivery catheter, filters of the present invention may be maintained in the delivery configuration by, for example, a removable suture that is removed once the filter is properly positioned within the patient's vessel. During deployment, an occlusion device, such as a standard balloon catheter, may be employed to arrest antegrade flow through the vessel, and thereby antegrade advancement of emboli, until the vascular filter is deployed.

Vascular filters of the present invention may be collapsed for retrieval within the guide wire lumens of conventional treatment devices, such as angioplasty catheters and stent delivery systems, thereby obviating the need to re-insert a specialized retrieval catheter to remove the vascular device. However, a retrieval sheath having a distal region that flares or expands outwardly to receive the emboli-filled recesses of the filter upon completion of an interventional procedure, may optionally be used in accordance with the present invention.

Methods of using embodiments of the present invention are also provided.

BRIEF DESCRIPTION OF THE DRAWINGS

Further features of the invention, its nature and various advantages will be more apparent from the following detailed description of the preferred embodiments, taken in conjunction with the accompanying drawings, in which like reference numerals refer to like parts throughout, and in which:

FIGS. 1A-1C are, respectively, a perspective view of a vascular filter constructed in accordance with the principles of the present invention in a deployed state, a cross-sectional view of the filter along section line A-A in FIG. 1A, and a side-sectional view of the filter along section line B-B in FIG. 1B;

DETAILED DESCRIPTION OF THE INVENTION

Figure 2A:
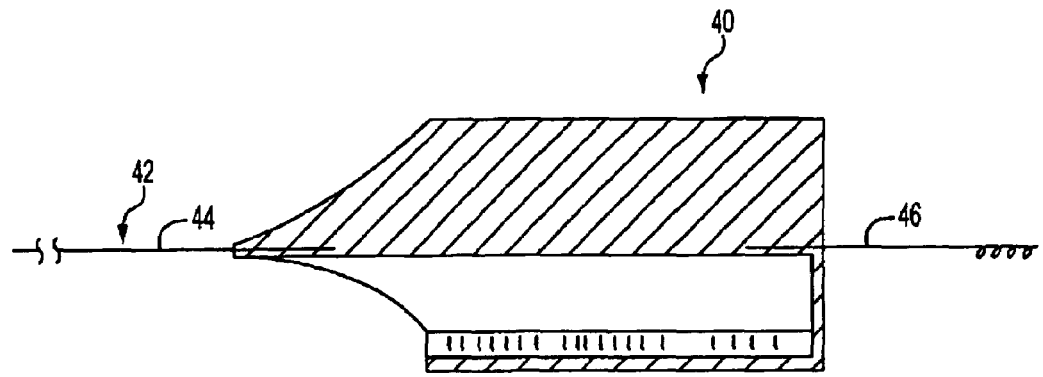
FIGS. 2A-2C are side-sectional views of alternative embodiments of the vascular filter of FIG. 1.

The present invention relates to methods and apparatus for filtering material from a body lumen. More particularly, the present invention provides a resiliently self-expanding foam filter adapted to capture and remove emboli, thrombus, and foreign bodies from a patient's vasculature.

With reference to FIG. 1, a first embodiment of apparatus in accordance with the present invention is described. Filter 10 comprises foam body 12 defining at least one bore or recess 14. In FIG. 1, foam body 12 is illustratively depicted with three recesses 14 separated by partitions 16, but any number of recesses may be provided, as will be apparent to those of skill in the art. Foam body 12 is coupled to a distal region of elongated member 18, which is preferably radiopaque. Filter 10 may also optionally comprise one or more radiopaque features (not shown) that facilitate positioning of the filter within a patient's vasculature. Elongated member 18 preferably comprises a standard guide wire.

Foam body 12 is fabricated from foam that is suited for both conformably sealing against a vessel wall and for capturing emboli within recesses 14. The foam is preferably open-celled having pores with a pore size that allows blood, but not dangerously sized emboli, to pass therethrough. Alternatively, the foam may be closed-celled, in which case pores may be manually formed, for example, by laser drilling. The pores preferably have a minimum diameter greater than approximately 5 μm, and a maximum diameter smaller than approximately 100 μm. More preferably, the pores have a diameter in a range of between about 60 and 80 μm.

In the context of this written description, the pores need not be spherical, but may be of any irregular shape. Accordingly, in this written description, a reference to the "diameter" of a pore refers to the average width of an external opening or the pore or an average diameter of an irregularly shaped void.

Porosity, i.e. the density of pores, within the foam may be specified to control a pressure drop across the vascular filter when used within a patient's vasculature. The foam is also preferably resilient or elastomeric, allowing the filter to self-expand from a collapsed delivery configuration to an expanded deployed configuration. Suitable foams may comprise, for example, foams fabricated from latex, silicone, or polymers, such as polyethylene, polyurethane, polycarbonate, polyvinyl chloride, polystyrene, polypropylene, and polyester.

Foam body 12 is preferably tubular, with partitions 16 that extend in a tapering fashion beyond proximal end 20 of recesses 14. The tubular shape of body 12 provides for contact of a substantial length of filter 10 against the interior of a patient's vessel, as compared to previously-known filter hoops, struts, etc. This substantial contact length is expected to distribute forces that are applied by the filter to the patient's vessel over a greater area, thereby reducing stress and a potential for injury to the vessel wall. The substantial length also provides a good seal against the vessel wall.

Additionally, during retrieval and/or repositioning of filter 10, the contact length of filter 10 acts as a linear bearing and is expected to reduce a risk of 'stiction', or torqued sticking, against the vessel wall that may occur if the wall is contacted over an insufficient linear distance. Stiction may make it difficult or impossible to remove an embolic filter without performing emergency cut-down surgery. To reduce stiction, the length of a filter between its proximal and distal points of contact with the vessel wall is preferably greater than or equal to about 1½ times the internal diameter of the vessel, and is even more preferably greater than about 2 times the internal diameter. Accordingly, for filter 10, the distance between proximal end 20 of recesses 14 and distal end 22 of the filter is preferably greater than about 1½ times, and even more preferably about 2 times, a maximum width of foam body 12.

As best seen in FIGS. 1B and 1C, recesses 14 extend within a substantial portion of foam body 12, thereby significantly reducing the solid volume of foam body 12 and facilitating contraction of filter 10 to a collapsed delivery configuration suited for intravascular delivery within small vasculature, for example, a delivery configuration of less than about 3 Fr. Additionally, the size and configuration of recesses 14 allow for effective capture of emboli, foreign bodies, and thrombus both large and small, while still allowing continued blood flow through distal end 22 of the filter.

As seen in FIGS. 1A and 1C, partitions 16 preferably taper proximally of recesses 14 to a point of union 17 having a cross-section that is just slightly larger than the diameter of elongated member 18. Elongated member 18 is coupled to foam body 12 of filter 10 along the line of union of partitions 16 extending distally from point of union 17. The tapering of partitions 16 provides a smooth, substantially continuous transition between the diameter of the elongated member and the maximum width of filter 10 that is expected to facilitate capture of filter 10 within a retrieval catheter with reduced force application. Additionally, the transition facilitates closure of proximal end 20 of recesses 14 prior to capture of recesses 14, thereby trapping emboli within the recesses and preventing escape of emboli during retrieval. Optionally, filter 10 also may be coated with a non-stick coating C that reduces friction during deployment and retrieval of the filter. Coating C may comprise, for example, a silicone or polytetrafluoroethylene coating.

Filter 10 may be manufactured using a variety of techniques. For example, a cylindrical section of open-celled foam of proper diameter may be cut to the length of filter 10, thereby forming a cylindrical plug. Closed-celled foam may alternatively be used, in which case pores may be manually formed within the foam, for example, by laser drilling.

Once a cylindrical plug has been cut, recesses may be bored into the plug from its proximal end to a position just proximal of its distal end. Side cuts are then made in the proximal region of the plug to form filter 10 with recesses 14 and tapering partitions 16. Finally, elongated member 18 is attached to the filter by drilling a small hole along the line of union of partitions 16. Elongated member 18 then is advanced through the drilled hole until filter 10 is disposed about the distal region of the elongated member. The elongated member is affixed to the filter, for example, with an epoxy or with a friction fit. Boring, cutting, and drilling operations may be achieved using standard equipment, per se known, or with a laser.

Referring now to FIG. 2, alternative embodiments of vascular filter 10 are described. In FIG. 2A, foam filter 40 is substantially equivalent to filter 10, except that elongated member 42 comprises proximal section 44 and distal section 46 that are gapped, or spaced apart from one another. Proximal section 44 is attached to filter 40 along the filter's proximal region, while distal section 46 is attached along the filter's distal region. Since elongated member 42 is not attached to, nor disposed within, a central region of filter 40, it is expected that filter 40 may be collapsed to an even smaller delivery profile than filter 10 of FIG. 1.

Figure 2B:
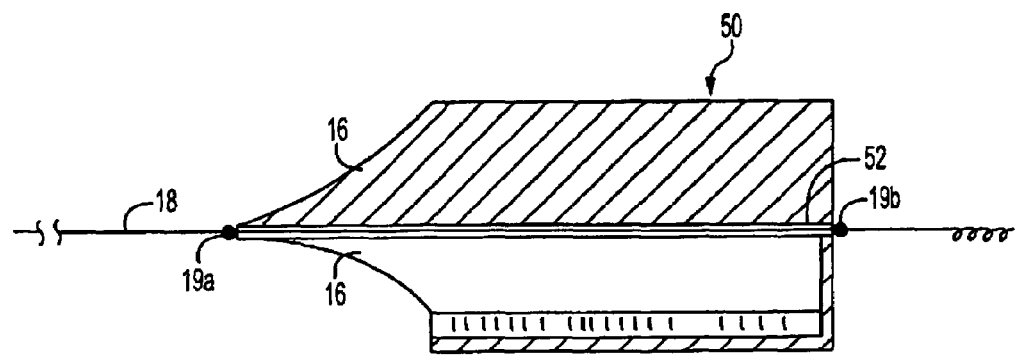

In FIG. 2B, filter 50 comprises lumen 52 that extends along the line of union of partitions 16. Elongated member 18 is disposed within lumen 52 and is provided with proximal and distal stops 19a and 19b, respectively, such as described in U.S. Pat. No. 6,179,859. Filter 10 is thus longitudinally restrained with respect to member 18; however, it may rotate independently of the elongated member. This is expected to facilitate advancement of filter 50 to a target site, as well as expansion, use, and retrieval of the filter, by allowing independent torqueing of elongated member 18. Stops 19 are preferably radiopaque to facilitate positioning of filter 10. Alternatively, as described in the aforementioned patent, elongated member 18 may include only a distal stop 19b, thereby allowing filter 10 to be advanced along elongated member 18 after the elongated member is placed in a vessel.

Figure 2C:
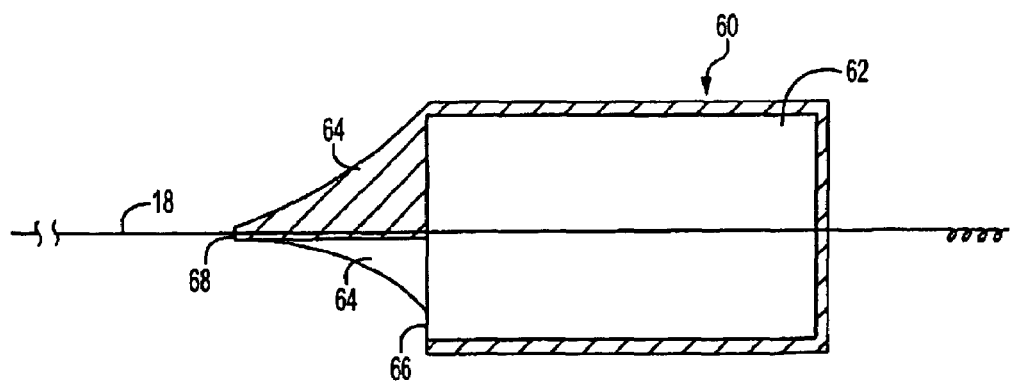

In FIG. 2C, filter 60 comprises solitary recess 62, and partitions 64 do not extend within the tubular portion of filter 60. Instead, the partitions only extend, and taper, from proximal end 66 of recess 62 to proximal point of union 68 of partitions 64. At point of union 68, partitions 64 have a cross-section that is just slightly larger than the diameter of elongated member 18. Thus, as with partitions 16 of filter 10, partitions 64 provide filter 60 with the smooth, substantially continuous transition between the diameter of the elongated member and the maximum width of filter 60 that facilitates capture of filter 60 with reduced force application, as well as closure at proximal end 66 of recess 62. However, since partitions 64 do not extend within the tubular portion of filter 60, it is expected that filter 60 may be collapsed to an even smaller delivery profile than filter 10. As will be apparent to those of skill in the art, within the tubular portion of filter 60, partitions 64 alternatively may extend just along their line of union (not shown), thereby reducing the volume of filter 60, while still providing attachment of elongated member 18 along the entire length of filter 60.

Figure 3:
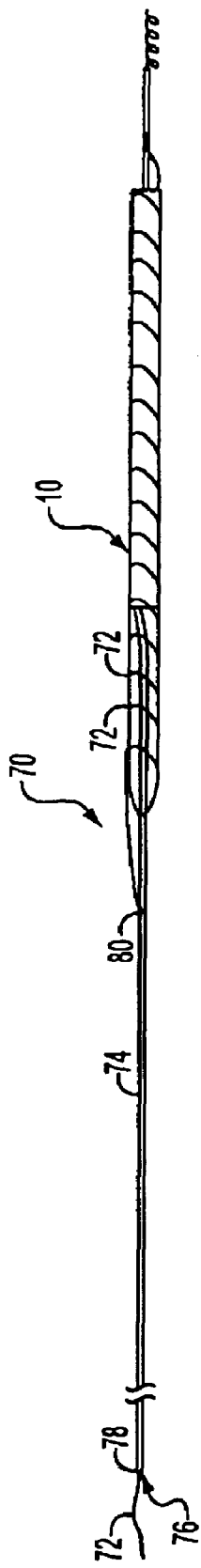
FIG. 3 is a side view of a delivery system for use with vascular filters of the present invention.
Figure 4:
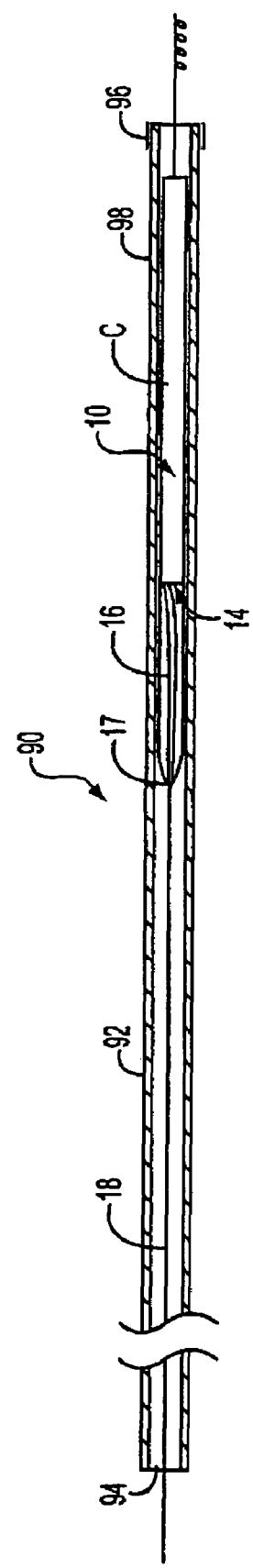
FIG. 4 is a side view, partially in section, of an alternative embodiment of the delivery system of FIG. 3.

With reference now to FIGS. 3 and 4, alternative delivery systems for filters of the present invention are described. The delivery systems are illustratively depicted in use with filter 10, but obviously filters 40, 50, or 60, or any other filter in accordance with the present invention, could be substituted for filter 10.

In FIG. 3, delivery system 70 comprises tear-away suture 72 that is wrapped about filter 10 to dispose the filter in a collapsed delivery configuration. Filter 10 is coupled to elongated member 74, which comprises lumen 76 that extends from proximal end 78 to through-hole 80. Suture 72 extends through lumen 76, out of through-hole 80, and around filter 10, and is then attached to elongated member 74 distal of filter 10. When filter 10 is positioned at a treatment site, a physician may pull on the proximal end of suture 72 to cut or tear away the suture, thereby releasing filter 10, which self-expands to its original, non-compressed, deployed configuration. Through-hole 80 of elongated member 74 may, for example, be sharp to facilitate cutting of the suture. Other techniques for releasing the suture will be apparent to those of skill in the art. Advantageously, delivery system 70 eliminates the need for an external sheath to deliver filter 10, thereby reducing the delivery profile of the system and allowing filter 10 to be delivered on a "bare" guide wire.

Referring to FIG. 4, an alternative delivery system for filters of the present invention is described. Delivery system 90 comprises delivery sheath 92 having lumen 94 extending therethrough. Sheath 92 may comprise a full-length sheath, as seen in FIG. 4, or may alternatively comprise a shorter sheath (not shown) sufficient for disposal of filter 10 therein. Sheath 92 preferably comprises radiopaque marker 96 along its distal region 98 that facilitates positioning of delivery system 90 at a treatment site. Alternatively or in addition to marker 96, sheath 92 may comprise a radiopaque marker disposed proximally of filter 10 (not shown) that facilitates, for example, easy determination of when the filter has been advanced past a stenosis.

Filter 10 is disposed in a delivery configuration within distal region 98 of sheath 92. This may be accomplished, for example, by advancing distal region 98 over the proximal end of elongated member 18 until proximal point of union 17 of partitions 16 of filter 10 abuts the distal end of sheath 92. Continued advancement of sheath 92 with respect to filter 10 causes the sheath to contact the tapered section of partitions 16, thereby gradually collapsing filter 10 to its delivery configuration and closing recesses 14.

A similar technique may be used to collapse filter 10 within a retrieval sheath after capture of emboli, thrombus, etc., within recesses 14. Optional coating C on the surface of filter 10 may facilitate loading of the filter within sheath 92, as well as deployment of the filter, by reducing friction between the sheath and the filter. Filter 10 may be deployed within a body lumen by retracting sheath 92 with respect to filter 10 so that filter 10 resiliently expands to the deployed configuration of FIG. 1. Alternatively, filter 10 may be deployed by advancing the filter with respect to sheath 92.

Optionally, delivery sheath 92 may be provided with an additional guide wire lumen (not shown) that permits a lesion to be crossed with an unencumbered guide wire prior to passage of filter 10. This is expected to reduce emboli generation during placement of filter 10. The additional guide wire lumen may be configured for "rapid exchange" use, and/or may simply comprise a hypotube attached to the exterior of sheath 92 along distal region 98.

During deployment of filter 10, an occlusion device (not shown), such as a standard balloon catheter, may be used in conjunction with, or as part of, the filter's delivery system. Such an occlusion device may be used with delivery systems 70 and 90, or with other delivery systems that will be apparent to those of skill in the art. The occlusion device may arrest antegrade flow through a vessel, thereby arresting antegrade advancement of emboli until filter 10 has been deployed to capture the emboli.

Referring now to FIG. 5, a method of using apparatus of the present invention is described. FIG. 5 are illustratively depicted with filter 10 and delivery system 90. However, alternative filters, such as filters 40, 50, and 60, or alternative delivery systems, such as delivery system 70, may also be used in accordance with the present invention. In FIG. 5A, filter 10 is disposed in a collapsed delivery configuration within distal region 98 of delivery sheath 92. Elongated member 18 extends within lumen 94 of the delivery sheath to a position proximal of the proximal end of the sheath.

Figure 5A:
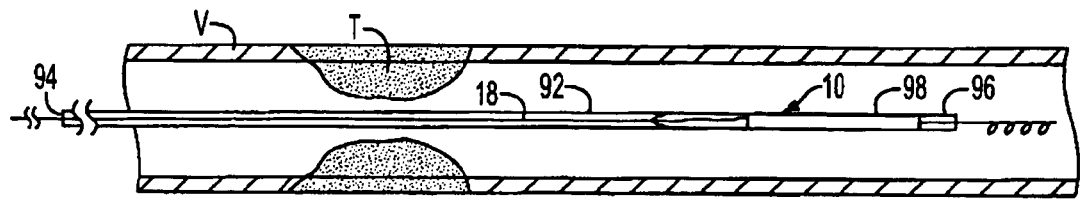
FIGS. 5A-5E are side sectional views depicting a method of deploying, using, and retrieving the vascular filter of FIG. 1 using the delivery system of FIG. 4.

As seen in FIG. 5A, distal region 98 of delivery sheath 92 is delivered to a position distal of a treatment site T within a patient's vessel V using, for example, well-known percutaneous techniques. The radiopacity of marker 96 may facilitate positioning of distal region 98 of delivery system 90, and thereby filter 10, distal of treatment site T. Alternatively, filter 10 or other portions of delivery system 90 may be radiopaque to facilitate positioning. Treatment site T may, for example, comprise a stenosed region of vessel V.

Figure 5B:
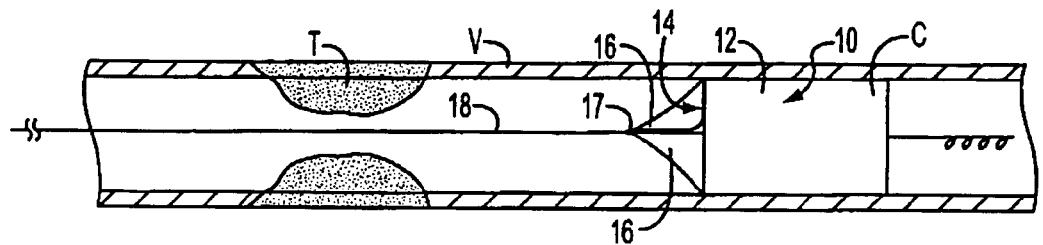

In FIG. 5B, delivery sheath 92 is retracted with respect to filter 10 to remove the sheath from the filter (filter 10 may alternatively be advanced with respect to sheath 92 in order to free the filter from the sheath). Filter 10 resiliently self-expands into sealing contact with the wall of vessel V. Recesses 14 open and are configured for capture of emboli, thrombus, foreign bodies, etc. The porosity of foam body 12 of filter 10 ensures continuous blood flow through filter 10 and vessel V. Sheath 92 is withdrawn from vessel V such that elongated member 18 is no longer disposed within lumen 94 of the sheath.

Figure 5C:
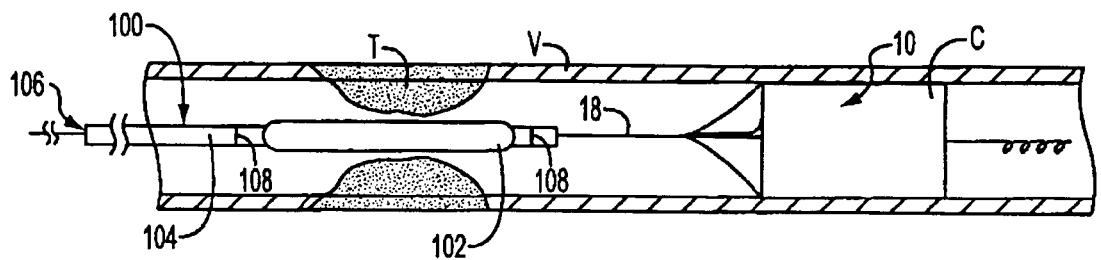

In FIG. 5C, balloon catheter 100, for example, a standard angioplasty catheter, comprises balloon 102 coupled to catheter shaft 104. Shaft 104 comprises guide wire lumen 106. The proximal end of elongated member 18 is passed through lumen 106, and balloon 102 of catheter 100 is advanced to treatment site T over the elongated member. Radiopaque marker bands 108 attached to the balloon facilitate positioning of the balloon at the treatment site.

Figure 5D:
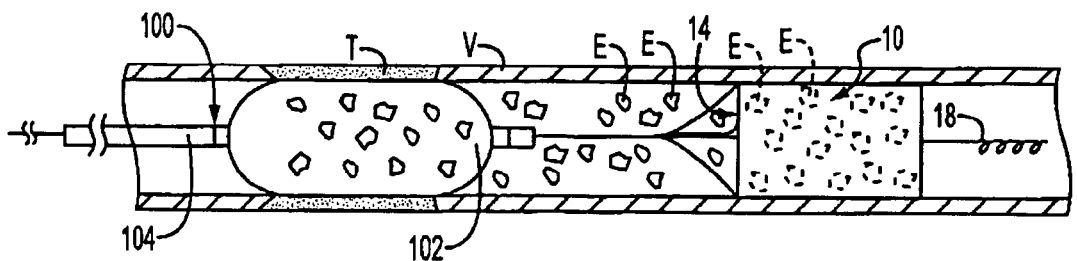

In FIG. 5D, balloon 102 is inflated to compress stenosis at treatment site T against the wall of vessel V to restore more normal blood flow through the vessel. The balloon is then deflated. Balloon 102 may be inflated and deflated multiple times, as required, to compress the stenosis. Compressing the stenosis generates emboli E that are carried downstream by antegrade blood flow. The emboli are captured within recesses 14 of filter 10.

Figure 5E:
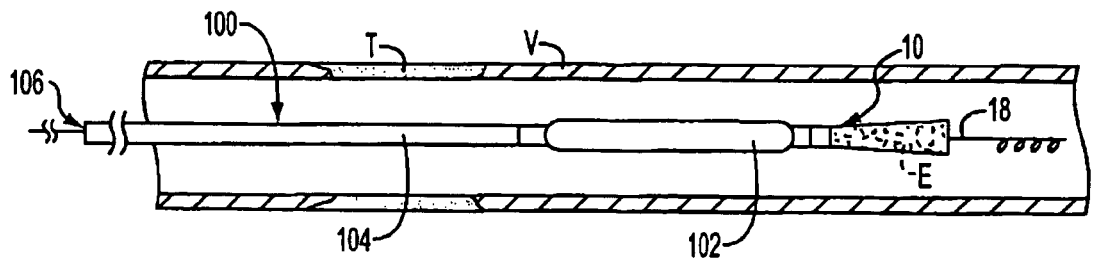

In FIG. 5E, filter 10 is collapsed for retrieval within guide wire lumen 106 of balloon catheter 100. This is accomplished by distally advancing catheter 100 with respect to filter 10 until the distal end of the catheter contacts proximal point of union 17 of partitions 16 (see FIG. 5B). Continued advancement of catheter 100 causes the sheath to contact the tapered section of partitions 16, thereby gradually collapsing filter 10 and closing recesses 14, which contain captured emboli E. Filter 10 may alternatively be collapsed by proximally retracting the filter with respect to catheter 100. Filter 10 may be drawn completely or only partially within guide wire lumen 106. Catheter 100, with filter 10 and emboli E disposed therein, is then removed from vessel V.

FIG. 5 illustratively demonstrate use of filter 10 in conjunction with an angioplasty procedure. Filters of the present invention also may be used in conjunction with a wide variety of other interventional procedures and devices, including stenting, thrombectomy, atherectomy, embolectomy, and foreign body removal devices, as well as others that will be apparent to those of skill in the art. In FIG. 5E, filter 10 is collapsed for retrieval within guide wire lumen 106 of balloon catheter 100. Alternatively, a specialized retrieval catheter may be used for capture of filter 10. Such a retrieval catheter may, for example, comprise a distal region that flares or expands outwardly to receive emboli-filled recesses 14 of filter 10 (not shown).

Although preferred illustrative embodiments of the present invention are described hereinabove, it will be evident to those skilled in the art that various changes and modifications may be made therein without departing from the invention.

For example, in addition to foam, filters of the present invention may also be fabricated from reversibly elastic materials, such as rubber, e.g. silicone rubber. In such embodiments, the filter would be biased to the expanded deployed configuration, and would then be stretched and folded to the collapsed delivery configuration. Alternatively, the filter could be fabricated from sintered spheres of material.

As yet another alternative, the filter may be made from a hollow or thin-walled tube of material, for example, polymeric material. Moreover, the foam filter and/or its partitions may be formed as a support hoop to which a filter sac is attached. Regardless of the fabrication technique or material, embodiments of the present invention preferably are biased to an expanded deployed configuration, but can be collapsed to a delivery configuration from which they self-expand to the deployed configuration. It is intended in the appended claims to cover all such changes and modifications that fall within the true spirit and scope of the invention.

What is claimed is:

1. An apparatus for distal protection during a medical procedure, the apparatus comprising a vascular filter having a body made of a resilient expandable foam allowing blood passage therethrough while preventing passage of particles above a predetermined size, the body including one or more recesses configured for capturing emboli.

2. The apparatus of claim 1, further comprising an elongated member having a distal region, wherein the vascular filter is coupled to the distal region.

3. The apparatus of claim 2, wherein the elongated member comprises a guide wire extending longitudinally through the body and coupled to the body.

4. The apparatus of claim 2, wherein the filter is longitudinally, but not rotationally, constrained with respect to the elongated member.

5. The apparatus of claim 2, further comprising a radiopaque feature coupled to the apparatus.

6. The apparatus of claim 2, further comprising an interventional device in communication with the apparatus.

7. The apparatus of claim 6, wherein the interventional device comprises a balloon catheter.

8. The apparatus of claim 1, wherein the foam comprises a sponge-like material having a multiplicity of pores.

9. The apparatus of claim 8, wherein the multiplicity of pores have a diameter greater than about 5 µm.

10. The apparatus of claim 9, wherein the pores have a diameter between 30 and 100 µm.

11. The apparatus of claim 10, wherein the pores have a diameter between 60 and 80 µm.

12. The apparatus of claim 1, wherein the foam comprises a foam fabricated from a material chosen from the group consisting of latex, silicone, polyethylene, polyurethane, polycarbonate, polyvinyl chloride, polystyrene, polypropylene, polyester, and combinations thereof.

13. The apparatus of claim 1, wherein the vascular filter has a length that is greater than or equal to 1½ times a maximum width of the filter.

14. The apparatus of claim 13, wherein the length of the vascular filter is greater than or equal to 2 times the maximum width of the filter.

15. The apparatus of claim 1, wherein the foam body defines a plurality of neighboring recesses and includes partitions disposed between the neighboring recesses.

16. The apparatus of claim 15, wherein the partitions have a line of union, the apparatus comprises an elongated member, and the filter is coupled to the elongated member along the line of union of the partitions.

17. The apparatus of claim 16, wherein the partitions taper proximal of the recesses.

18. The apparatus of claim 1, wherein the filter is resiliently expandable from a collapsed delivery configuration adapted for use with a delivery system, to an expanded deployed configuration adapted for engagement with the interior wall of a patient's vessel.

19. The apparatus of claim 18 further comprising a delivery system having a delivery sheath, the filter disposed in a collapsed delivery configuration within the delivery sheath.

20. The apparatus of claim 18 further comprising a delivery system having a removable suture, the suture disposed about the filter to maintain the filter in the delivery configuration.

21. The apparatus of claim 18, wherein a proximal end of the one or more recesses is closed when the filter is in the collapsed configuration, thereby preventing emboli captured within the recesses from escaping.

22. The apparatus of claim 1, wherein the filter further comprises a non-stick coating.

23. The apparatus of claim 22, wherein the non-stick coating is chosen from the group consisting of silicone and polytetrafluoroethylene.

24. Apparatus for distal protection during a medical procedure, the apparatus comprising a vascular filter having a resiliently expandable body defining one or more recesses adapted for capturing emboli, wherein the body comprises a material selected from the group consisting of foam, resiliently elastic materials, rubber, silicone rubber, latex foam, urethane foam, the material allowing blood passage therethrough while preventing passage of particles above a predetermined size.

25. The apparatus of claim 24, further comprising a filter material attached to the resiliently expandable body to filter material passing into the one or more recesses.

* * * * *